United States Patent [19]

Jerath

[11] Patent Number: 5,222,485
[45] Date of Patent: Jun. 29, 1993

[54] ULTRASOUND LABOR MONITORING METHOD AND APPARATUS

[76] Inventor: Ravinder Jerath, 2100 Central Ave., Augusta, Ga. 30903

[21] Appl. No.: 583,088

[22] Filed: Sep. 17, 1990

[51] Int. Cl.$^5$ .............................................. A61B 8/12
[52] U.S. Cl. ........................... 128/660.01; 128/662.06
[58] Field of Search ............... 128/775, 662.03–662.04, 128/662.06

[56] References Cited

U.S. PATENT DOCUMENTS

| | | | |
|---|---|---|---|
| 4,579,123 | 4/1986 | Chen et al. | 128/662.03 |
| 4,593,699 | 6/1986 | Poncy et al. | 128/662.03 |
| 4,722,346 | 2/1988 | Chen | 128/662.03 |
| 4,757,823 | 7/1988 | Hofmeister et al. | 128/662.06 X |

OTHER PUBLICATIONS

Taylor, W. B. et al "A High-Resolution Transrectal Ultrasonographic System", UTS in Med & Biol., vol. 5, pp. 129–138 1979.

*Primary Examiner*—Francis Jaworski

[57] ABSTRACT

An obstetrical device is provided for use during labor and childbirth to determine and monitor accurately the position of a fetal head and the configuration of the cervix using ultrasonographic techniques. The device comprises an elongated inflatable latex rubber sac closed at one end by a latex rubber diaphragm that is supported by a resilient peripheral ring. In use, the device is inserted into the birth canal with a portion of the sac positioned in the vaginal cavity, a portion extending through the cervical canal and with the diaphragm positioned in the uterus adjacent the fetal head. The diaphragm is maintained in the uterus by the flexible peripheral ring, which has a diameter greater than that of the cervical canal. With the device thus positioned, it is inflated with a saline solution causing it to expand, bear against, and take the shape of the vaginal cavity, uterus, and fetal head. A longitudinal ultrasonographic image taken from just outside the vagina, then, clearly reveals the interface between the saline solution and surrounding tissue and thus the configuration of the cervix and station of the fetal head for accurate measurement directly from the ultrasound image.

16 Claims, 5 Drawing Sheets

ULTRASOUND LABOR MONITORING METHOD AND APPARATUS

TECHNICAL FIELD

This invention relates to medical obstetrics and particularly to the application of ultrasonographic techniques for monitoring the progress of labor during childbirth.

BACKGROUND OF THE INVENTION

During labor and childbirth, a number of physiological conditions of mother and infant typically are monitored by the attending obstetrician to determine precisely when and how the infant is to be delivered. Among the most important of these conditions are the magnitude and rate of cervical dilatation, the extent to which the cervical walls have thinned or effaced and the rate of such effacement, and the longitudinal position or station of the baby's head within the birth canal. Obviously, the reliability and accuracy of the determination of these factors can be very important since the critical decisions of when to deliver the infant and whether or not to deliver the infant by cesarian section are commonly made based on such determinations.

While medical science has made great strides in recent decades, very little progress has been made in methods of determining and monitoring the conditions of the cervix and the station of an infant's head during labor. Generally, these factors are still determined as they have been for decades through manual insertion of the doctor's or nurse's fingers through the vagina for physical examination and estimation of the condition of the cervix and infant. This method, however, has long been plagued with persistent inherent problems that can and sometimes do result in untimely delivery of the infant and can even result in the performance of unnecessary cesarian sections. These problems persist largely because the accuracy and reliability of estimates based on physical examinations are highly dependent upon the experience or even the finger size of the attending doctor or nurse. Widely varying estimates of dilatation, effacement, and station can thus be obtained depending upon who conducts the examination. This problem is often exacerbated where two or even more attendants conduct cervical examinations in the course of labor to establish dilatation and effacement rates since the resulting Friedman curves, upon which many decisions and prognoses of labor related problems are based, become virtually meaningless. It can thus be seen that an almost total lack of objectivity and standardization exists among obstetricians and obstetric attendants in the determination and monitoring of the conditions of the cervix and station of the baby during labor.

Additional problems and shortcomings inherent in prior art manual examinations include the greatly increased risk of uterine or vaginal contamination and infection that can result from repeated examination, discomfort to the mother, risk of injury to the infant through breakage of fetal membranes, and the accidental dislodging of fetal monitors that are often secured to the baby's head to monitor fetal heartbeat.

In recent years, the techniques of ultrasonographic examination of the body's internal organs without physical intrusion into the body cavity has found widespread application in the medical community including the disciplines of obstetrics and gynecology. Indeed, ultrasound examinations have proven invaluable in the diagnosis of abnormal conditions of the cervix during pregnancy such as, for example, cervical incompetence.

Ultrasound examinations of the cervix and female reproductive system are traditionally carried out using the filled bladder method described by Sarti, et al[1] wherein the patient's bladder is at least partially filled with a saline solution causing it to enlarge and conform to the shape of surrounding uterine and cervical tissue. The difference in sonic density between the saline solution and surrounding tissue, then, renders the cervical outline clearly visible on an ultrasound image such that diagnosis and prognosis can easily be made.

[1] Sarti D A, Sample W F, Hobel C J, Staisch K J, *Ultrasound Visualization of a Dilated Cervix During Pregnancy,* Radiology 1979; 13:417.

Unfortunately, ultrasound techniques that have become successful in diagnosing abnormal conditions of the uterus during pregnancy have not, as a general rule, proven themselves useful in monitoring the conditions of the cervix and station of the fetal head during labor itself. This is due in part to the thinning of the cervical tissue during labor and to the substantially homogenous sonic density of the cervix and surrounding tissue, all of which renders the cervix and the relationship of the fetal head thereto indistinct in ultrasound images. Further, the filled bladder method of visualizing the cervix in the course of pregnancy is generally inapplicable during labor since the pressure of the inflating fluid within the bladder can deform the uterus and cervix and interfere with normal delivery of the infant. As a consequence, traditional manual examinations with their attendant inaccuracies, problems, and risks continue to be employed by obstetricians throughout the world for monitoring the progress of labor.

Thus, it is seen that a continuing and heretofore unaddressed need persists for a method of examining the cervix ultrasonically during labor and of monitoring the progress of its dilatation and effacement. Such a method should provide objective standardized and accurate indications of the cervical condition as well as the station of the infant's head with a minimum of physical intrusion and risks to mother and infant. It is to the provision of such a method and an apparatus for facilitating performance thereof that the present invention is primarily directed.

SUMMARY OF THE INVENTION

The present invention comprises a method and apparatus for use in the ultrasonographic determination and monitoring of the position or station of the fetal head and the configuration of the cervix during labor. The apparatus includes an elongated latex rubber body adapted to be inserted within the vaginal cavity. A latex rubber diaphragm supported by a resilient peripheral ring closes one end of the body. The other end of the body is closed and includes a flexible tube that communicates with the interior of the body and extends generally longitudinally a predetermined distance therefrom.

In practice, the apparatus is inserted by a doctor into the birth canal with the diaphragm and its supporting ring positioned within the uterus just inside the cervix, the elongated body of the apparatus positioned within the vaginal canal, and the flexible tube and lower portion of the body extending outside the mother's body. With the apparatus thus positioned, it can be inflated with an inflating fluid such as, for example, sterilized saline solution by injecting such fluid through the flexible tube with a syringe or the like. As the apparatus inflates, the walls of its elongated body expand and come to bear against and conform to the shape of the interior walls of the vaginal cavity. Similarly, the upper portion of the body, which extends through the mouth of the cervix, comes to bear against and conforms to the shape and size of the cervix and cervical canal. Similarly, the diaphragm within the uterus expands to bear against and conform to the shape of the fetal head, which typically is located adjacent to the cervical opening within the uterus. In this regard, the resilient ring, which supports the diaphragm and joins it to the walls of the elongated body, maintains the diaphragm in position within the uterus by yieldably lodging itself against the uterine walls surrounding the cervical canal opening.

It can thus be seen that the walls of the fully inflated apparatus bear against and conform to the shape of the interior walls of the vaginal cavity, the cervix and cervical canal, and the fetal head within the uterus. An interface is thus created between these surfaces and the saline solution within the apparatus with the interface taking on the configuration of the surfaces against which it bears. Since the sonic density of the saline is different than that of the surrounding tissue, a longitudinal ultrasonic image taken from just outside the vagina clearly reveals the interface and thus the shape and size of the cervix as well as the position of the fetal head with respect thereto. An attending doctor or nurse can then take periodic measurements of the dilatation and effacement of the cervix as well as the station of the infant's head directly from the ultrasound image. Further, a sequence of ultrasound images can be videotaped and reviewed at varying speeds by attending physicians to monitor the progress of labor in a way that has simply not been feasible in the past.

Thus it is seen that a unique ultrasound technique and apparatus for monitoring the progress of labor is now provided that is accurate, reliable and not dependant upon the skill or experience of an attending doctor or nursing staff. Precise and standardized determination of proper delivery time as well as the necessity of cesarian section in some cases is thus possible. Further, the method is virtually non intrusive since no further insertions are necessary once the device is properly inserted and inflated within the birth canal. Risks of vaginal infection or contamination and risks of injury to the fetus itself are therefore substantially eliminated.

These and many other features, objects and advantages of the present invention will become more apparent upon review of the following detailed description when taken in conjunction with the accompanying drawings.

DETAILED DESCRIPTION OF THE PREFERRED EMBODIMENTS

Figure 1:
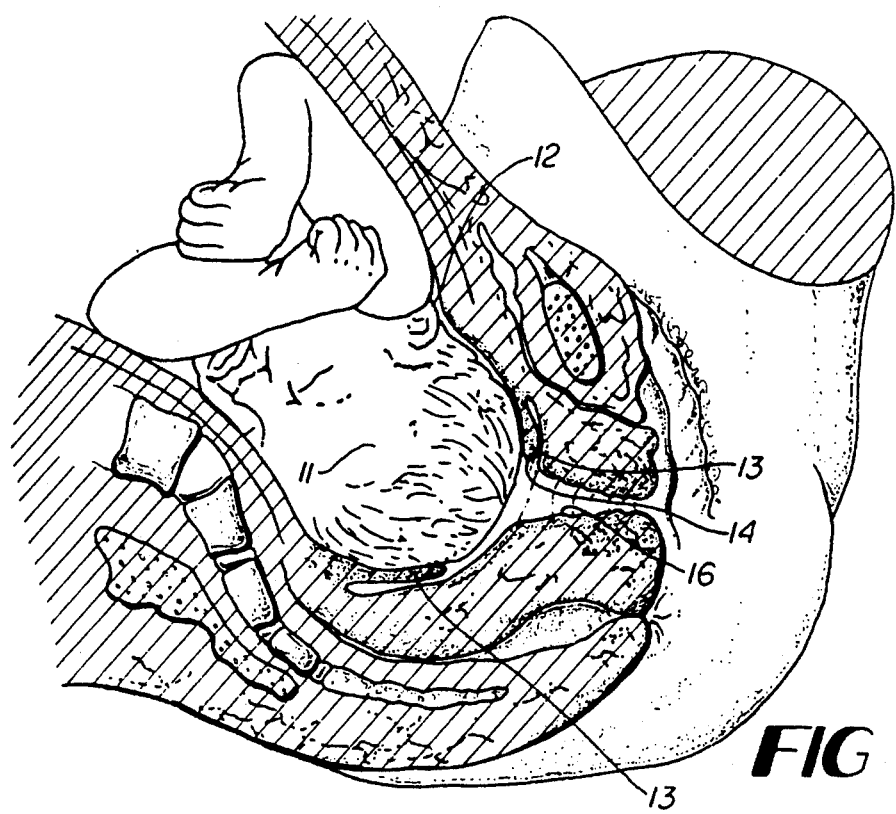
FIG. 1 is a partially cut-away view depicting an infant prepared for delivery within the uterus and showing the vaginal walls, the cervix, and the baby's head.

Referring now in more detail to the drawings, in which like numerals refer to like parts throughout the several views, FIG. 1 illustrates the typical position of an infant or fetus within the womb during labor. The fetus 11 is seen to be positioned within the uterus 12 with its head in a downward orientation in preparation for delivery. The cervix 13, which defines the entrance to the uterus, is seen to be partially dilated and effaced in preparation for passage of the infant from the uterus. The dilated cervical canal 14 opens into the vaginal cavity 16 which, in turn, communicates with the outside world.

Figure 2:
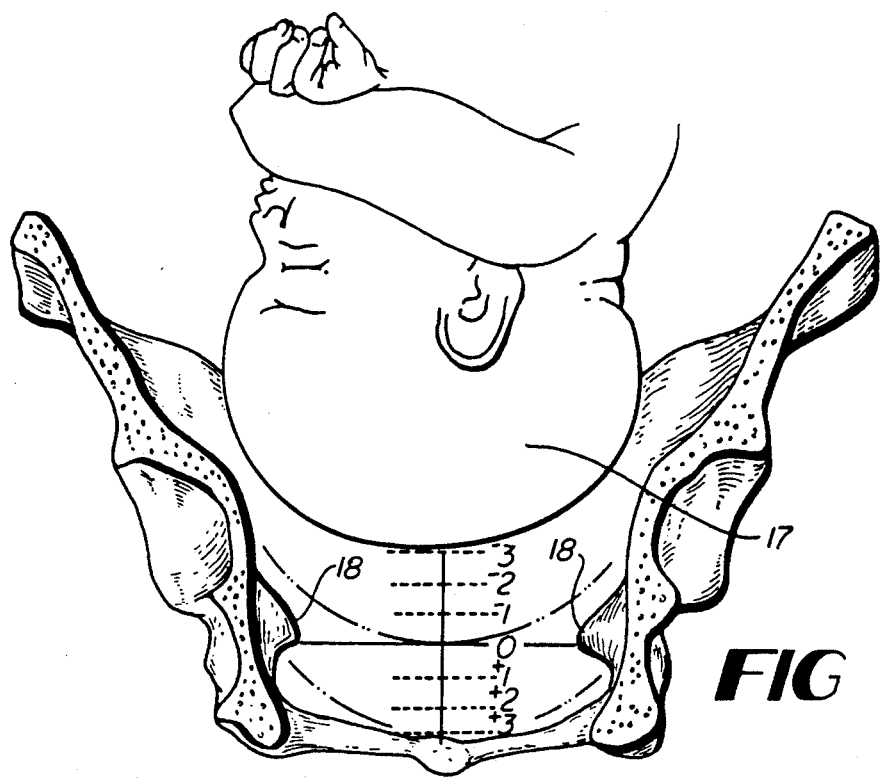
FIG. 2 is a perspective illustration of an apparatus that embodies principals of the invention in a preferred form.

During labor, the fetal head moves slowly downwardly from the uterus toward the vaginal cavity in preparation for delivery. The various positions of the fetal head during such movement are designated by station number as illustrated in FIG. 2. The infant is considered to be positioned at station 0 when the crown of its head 17 is located even with the mother's ischial spines 18. Stations above and below the zero station are designated in centimeters with station number −2, for example, indicating that the crown of the infant's head is 2 centimeters above the zero station while station number +2 indicates a position 2 centimeters below the zero station. In general, an infant is considered ready for delivery when the crown of its head is located at station number +3 or greater.

Figure 3:
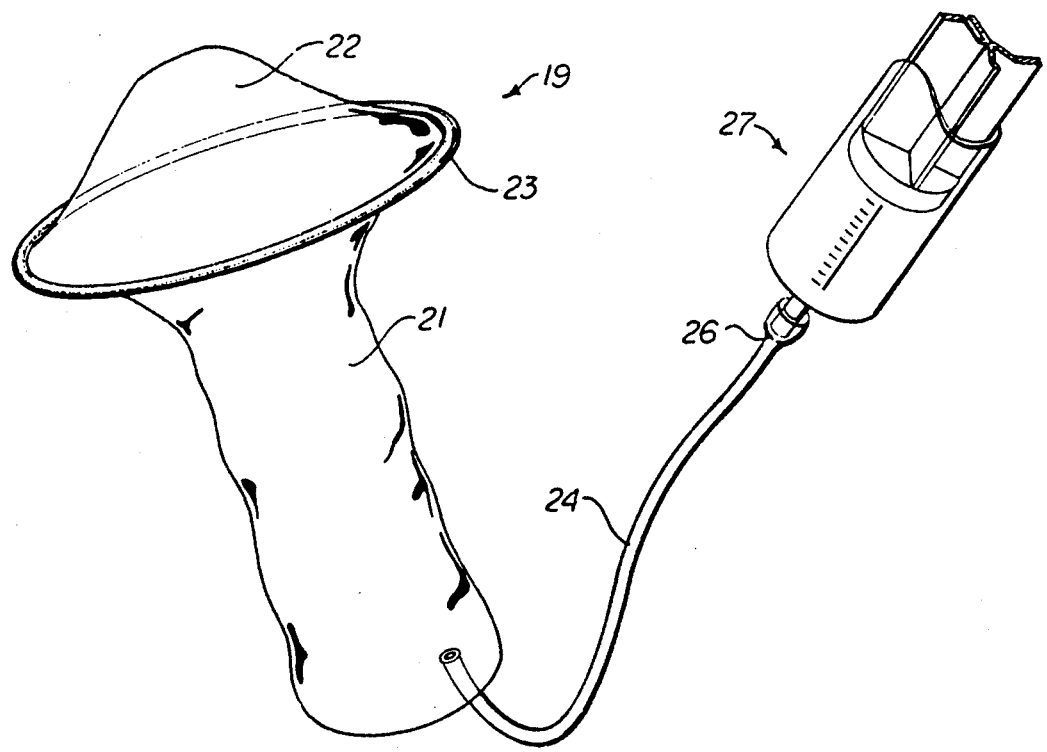
FIG. 3 is a partially cut-away view illustrating the various stations of an infant's head as it moves through the birth canal during delivery.

FIG. 3 illustrates the apparatus of the present invention in one preferred embodiment thereof. The apparatus 19 is seen to comprise an elongated body 21 in the form of a flexible inflatable sac that is preferably formed of thin latex rubber or the like. A flexible diaphragm or membrane 22, which is also preferably made of latex rubber is formed at and closes off one end portion of the body 21. A resilient, collapsible, peripheral ring 23 bounds and supports the diaphragm 22 at the end of the body 21.

The lower end portion of the body 21 is closed and a flexible tube 24, which communicates with the interior of the apparatus 19, is secured to and extends therefrom. The distal end 26 of the tube 24 is formed to receive the tip of a syringe 27 or other aspirating device for introduction of an inflating fluid through the tube 24 and into the apparatus 19.

In the embodiment of FIG. 3, the peripheral ring 23 is preferably formed of a solid or rolled latex rubber material such that the ring 23 and diaphragm 22 can be easily collapsed between an attending physician's fingers or within an ancillary insertion device for insertion through the cervical canal and into the uterus. Once in the uterus, the ring 23 can be released to expand under the influence of its resiliency and thus secure the diaphragm 22 in position within the uterus adjacent to the crown of the infant's head.

Figure 4:
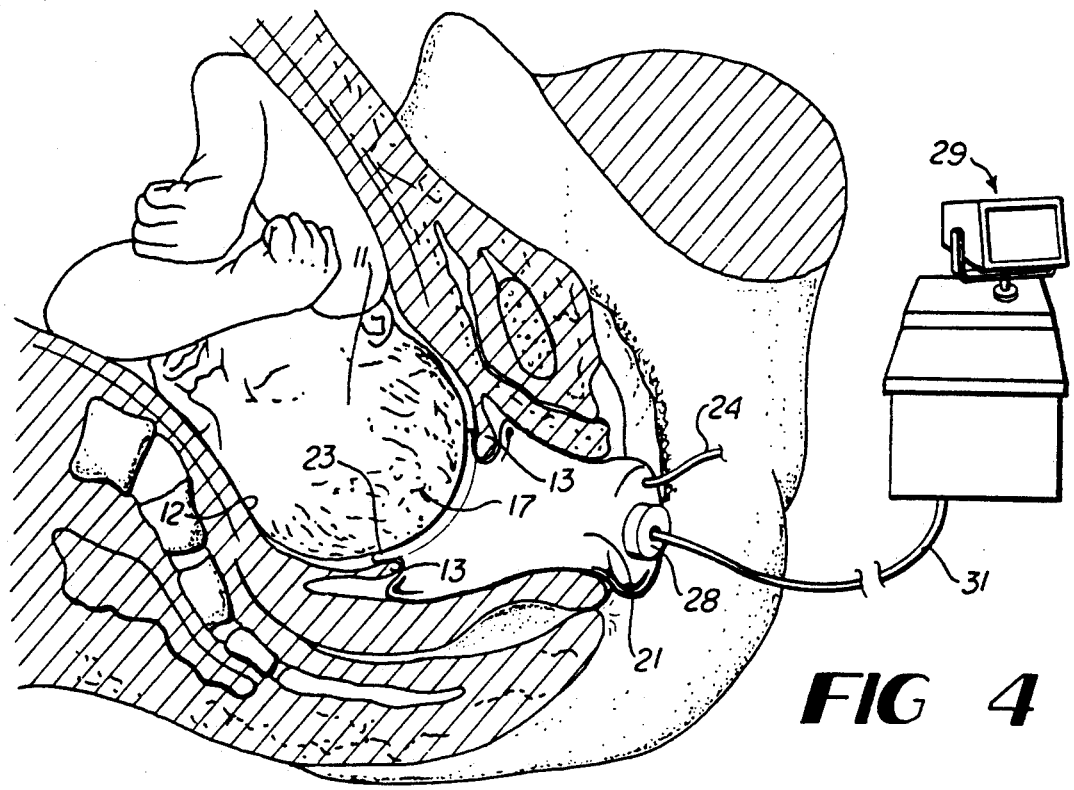
FIG. 4 is a partially cut-away elevational view showing a fetus within the uterus with the device of the present invention positioned and inflated within the birth canal.
Figure 5:
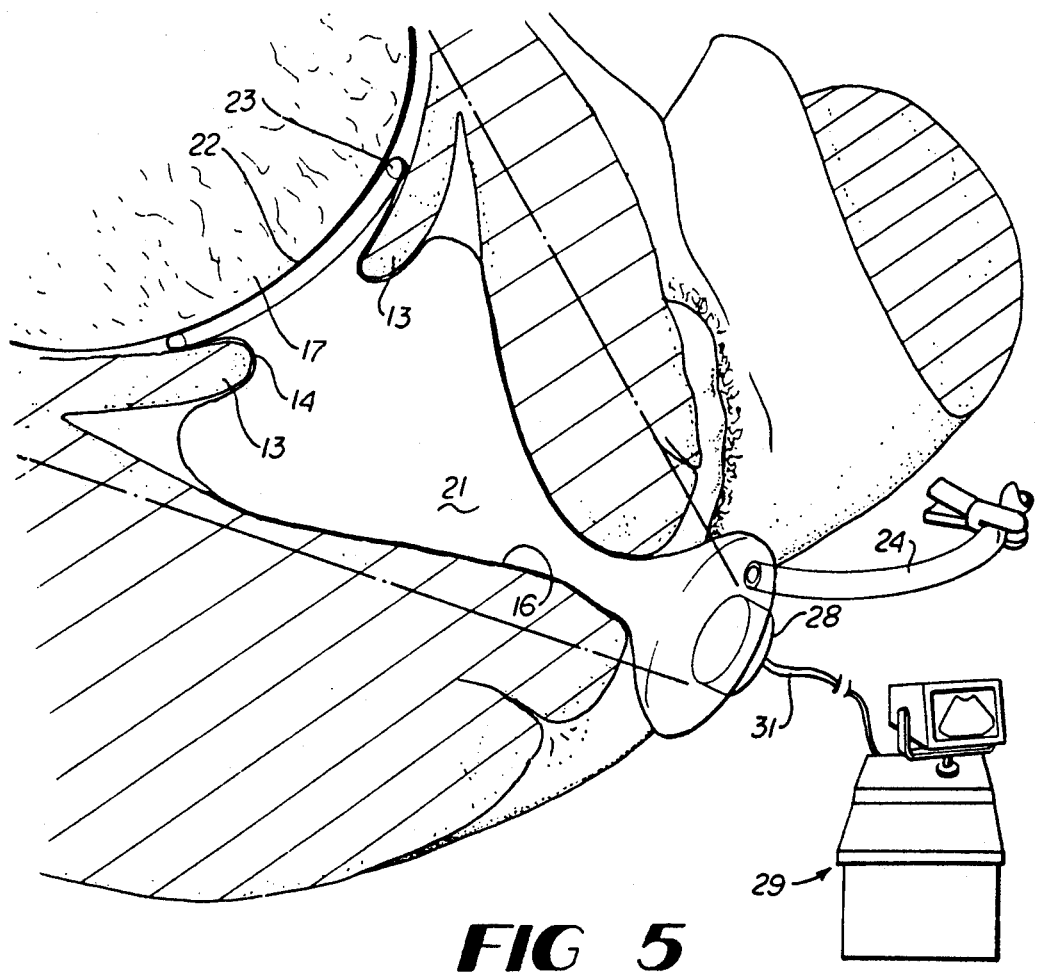
FIG. 5 illustrates the apparatus of the present invention inserted and inflated within the vagina and uterus with its walls bearing against and conforming to the shape of the interior walls of the vagina, the cervical canal and the fetal head.

FIGS. 4 and 5 illustrate the apparatus of FIG. 3 as it appears when inserted into the birth canal and inflated for ultrasonographic examination according to the method of the present invention. The apparatus is seen to be positioned with the mid-section of its body 21 positioned within the vaginal cavity, the upper end section of the body 21 extending through the cervical canal 14, and with the lower section of the body 21 extending through the vagina and outside the mother's body. The diaphragm 22 is positioned within the uterus 12 adjacent to the crown of the infant's head 17. The flexible peripheral ring 23 bears against the walls of the uterus just inside the opening of the cervical canal to support and secure the diaphragm 22 in position within the uterus 12.

The apparatus is seen in FIGS. 4 and 5 to have been inflated such that its body 21 bears against and conforms to the shape of the vaginal cavity, the cervix, and the cervical canal. Similarly, the pressure of the inflating fluid causes the diaphragm 22 to bear against and conform to the shape of the crown of the fetal head 17. While various inflating fluids might be used to inflate the apparatus of this invention, it is important that the fluid be chosen to have a sonic density different from that of the tissue of the birth canal and the baby's head so that a clear sonographic image can be obtained. In this regard, it has been found that a simple saline solution satisfies this criteria conveniently as such solutions are readily available to physicians in a typical delivery room setting.

An ultrasound transducer 28 is shown secured to the lower end portion of the body 21 outside the mother's body with the transducer 28 being electrically coupled to an ultrasound imaging system 29 by means of a transmission cable 31. The transducer 28 and imaging system 29 are of commonly available construction. Further, while the transducer 28 is illustrated as being secured to the apparatus 19 for providing a longitudinal ultrasound image, it will be understood that the transducer could be applied to the mother's body at various positions displaced from the vagina depending upon the needs of the particular attending physician and the circumstances of the labor. The positioning of the transducer 28 in FIGS. 4 and 5, therefore, is for illustration only and should not be construed as a restricting feature of the present invention.

Figure 7:
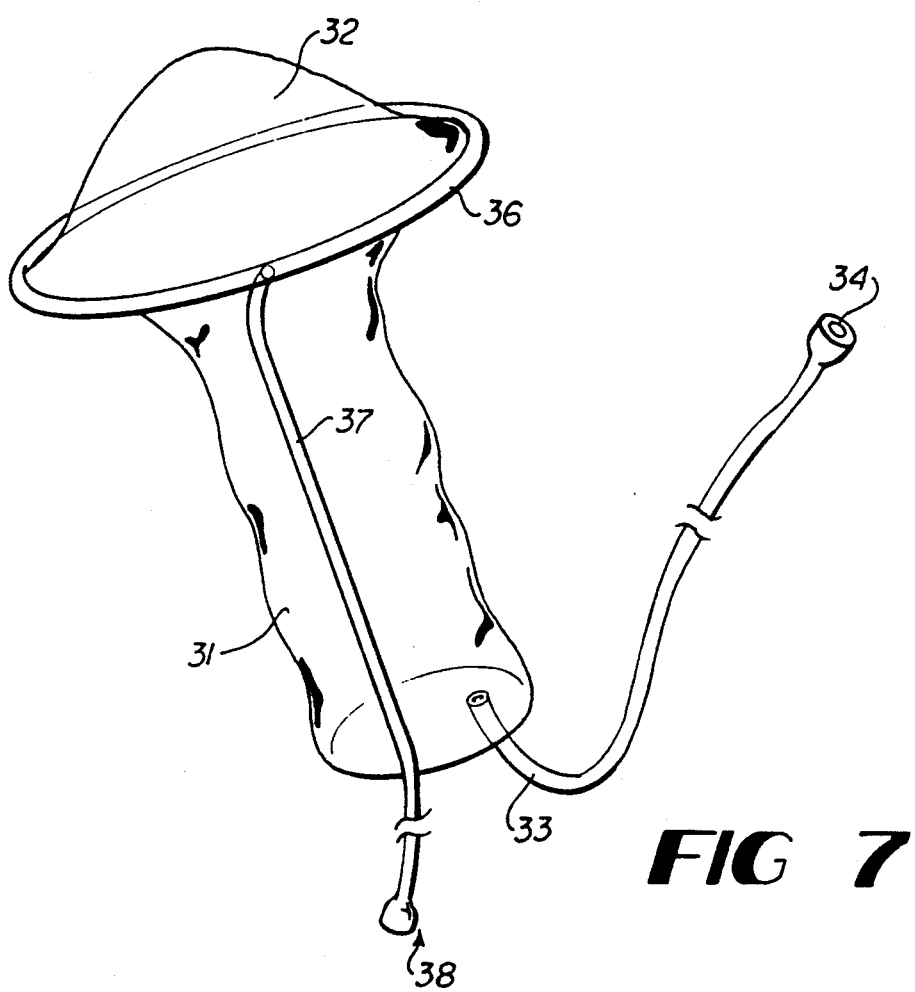
FIG. 7 is a perspective view of an apparatus that embodies principles of the invention in a second form.

FIG. 7 illustrates an alternate embodiment of the apparatus of the present invention. This embodiment is seen to comprise an elongated inflatable body 31 closed at its upper end by a flexible diaphragm 32. The lower portion of the body 31 is closed and a flexible tube 33, which communicates with the interior of the body 31, extends therefrom to a distal end 34 configured to receive an inflating fluid for inflation of the apparatus.

An hollow annular tube 36 bounds and supports the diaphragm 32 at the upper end of the body 31. An inflating tube 37 communicates with the interior of the annular tube 36 and extends along the body 31 to a distal end portion 38 adapted to reside outside the mother's body and configured to receive an inflating fluid from a source such as a syringe. With this configuration, fluid, such as a saline solution, can be introduced into the hollow annular tube 36 to inflate and expand the tube to a flexible ring shape for securing the diaphragm in position within the uterus. In this way the hollow ring 36 and diaphragm 32 are easily collapsed for insertion through the cervical canal and into the uterus, where the tube 36 can be inflated with a common syringe causing it to expand to its annular configuration and secure the diaphragm 32 within the uterus. In this regard, the distal end 38 of the tube 37 is preferably formed with a valve for closing communication through the tube 37 to maintain the inflated annular tube 36 in a ring-shaped configuration within the uterus. For removal of the apparatus, the valve can simply be opened to draw the fluid from the ring 36 thereby collapsing it and allowing the entire apparatus to move freely out of the birth canal.

OPERATION

In using the apparatus of the present invention for ultrasonographic monitoring of the progress of labor, an attending physician or nurse, using sterile gloves or the like, collapses the diaphragm and its supporting flexible ring between the fingers and manually inserts them through the cervical canal and into the uterus adjacent to the head of the infant. With the ring and diaphragm thus located, they are simply released whereupon the flexible ring expands to its annular shape under the influence of its resiliency to bear against the lower inner walls of the uterus just inside the cervical canal opening as best seen in FIG. 5. The diaphragm is thus securely but removably secured by its peripheral ring within the uterus adjacent to the crown of the infant's head.

With the diaphragm thus secured, the body of the apparatus extends from the ring within the uterus, through the cervical canal, and through the vaginal cavity to a location outside of the mother's body. The apparatus can then be inflated with a saline solution or the like by means of the inflating tube 24 such that its walls expand to bear against and conform to the shape of the vaginal cavity, the cervix, and the cervical canal. Similarly, the pressure of the inflating fluid causes the diaphragm to bear against and conform to the shape of at least a portion of the infant's head within the uterus. The inflating tube can then be closed off with a clamp or the like to maintain the apparatus in its fully inflated condition as best illustrated in FIG. 5.

With the apparatus thus inserted and inflated, the attending physician can secure an ultrasonic transducer to the lower end portion of the body just outside the vagina with the transducer being operatively coupled to an ultrasound imaging system. Periodic ultrasound images can then be made of the womb and infant therein for determining and monitoring the station of the infant and condition of the cervix. More specifically, since the sonic density of the inflating fluid is different than that of the surrounding tissue, the interface between such fluid and tissue generates an echo which appears as light contoured lines on the ultrasound image. Further, since such interface conforms substantially to the shape of the vaginal cavity, cervix, cervical canal and infant's head, the resulting ultrasound image shows a clear outline of these structures. Precise measurements of the magnitude of dilatation and effacement of the cervix as well as the station of the infant's head can then be made directly from the ultrasound images. Guess work inherent in prior art manually examinations is thus eliminated. Further, a series of ultrasound images can be made automatically at regular intervals and recorded on video tape for subsequent sequential review by an attending physician to determine the progress and nature of labor and to decide the proper time and method of delivery. Such tapes could also prove useful in later medical research or training since precise progressive images of the behavior of the cervix and infant during labor could be studied. These tapes might also prove useful as legal evidence in the event of subsequent malpractice or other claims related to the delivery.

Figure 6:
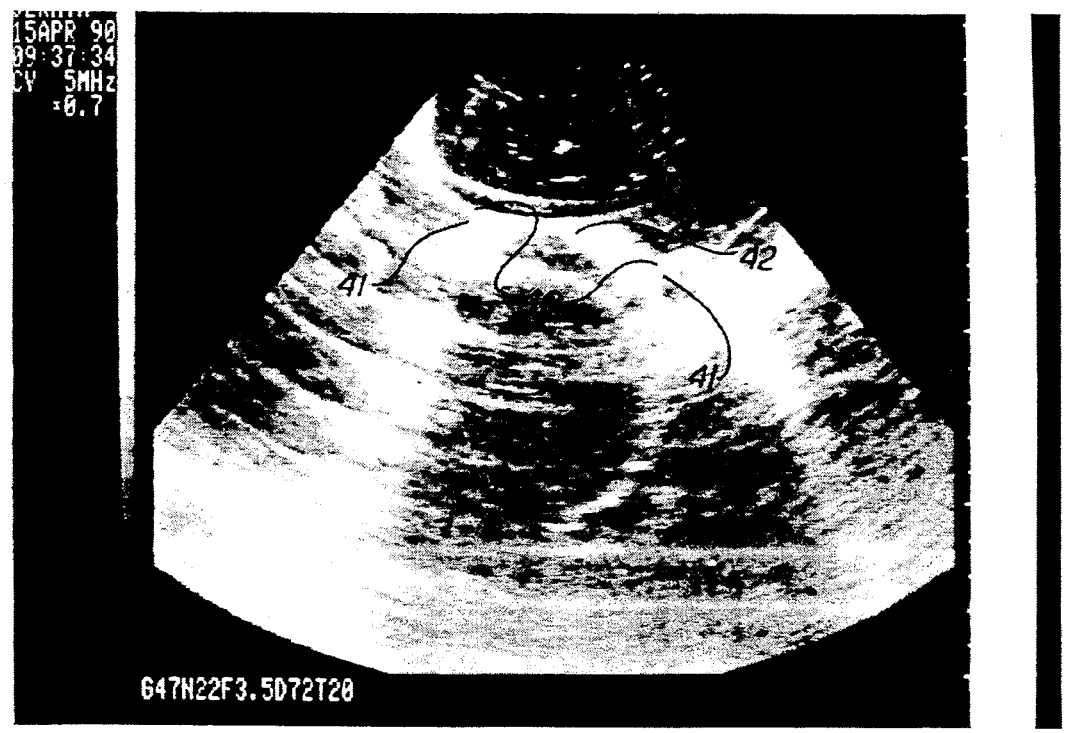
FIG. 6 is an ultrasound image of the type resulting from application of the method of this invention showing clear depiction of the cervix, vaginal walls and fetal head.

FIG. 6 is an actual longitudinal ultrasonographic image produced with the method and apparatus of the present invention applied to a model of the birth canal and a model fetus therein. As can be seen, the outline of the cervix 41, the cervical canal 40, and the crown of the fetal head 42 are clearly visible for measurement and monitoring. Just prior to delivery, the apparatus of the present invention can be removed easily by draining the inflating fluid therefrom and simply pulling it gently from the birth canal.

The invention has been described in terms of preferred embodiments. It will be understood, however, that various modifications and other configurations of the preferred embodiments might be made within the scope of the invention. The method, for example, has been described with reference to ultrasound imaging of the structures within the womb during labor. The invention might well be suited, however, to ultrasound imaging of various other structures within the body such as, for example, tumors within the colon. The invention should not therefore be considered limited to its uses in obstetrical and gynecological practices. These and many other modifications, deletions and additions might be made to the illustrated and preferred embodiments by persons of skill in the art without departing from the spirit and scope of the invention as set forth in the claims.

I claim:

1. An apparatus for use in the ultrasonographic determination and monitoring of the position of a fetal head and the configuration of the cervix during labor, said apparatus comprising:
   an elongated flexible member adapted to be inserted within the vaginal cavity with said elongated flexible member being expandable upon inflation to bear against and conform to the interior shape of the vaginal cavity;
   a diaphragm closing one end of said elongated member with said diaphragm being adapted to be inserted through the cervical canal and into the uterus to bear against the fetal head when said elongated member is inflated; and
   means for introducing and inflating fluid into said elongated member;
   said means for maintaining said diaphragm in position within the uterus comprising a resilient peripheral ring bounding and supporting said diaphragm at said one end of said elongated member with said ring being sized to nestle within the uterus surrounding the cervical canal opening therein.

2. An apparatus as claimed in claim 1 wherein said resilient peripheral ring is formed of latex rubber and adapted to be collapsed for insertion of said ring and said diaphragm through the cervical canal and to re-expand within the uterus to secure the diaphragm in position therein.

3. An apparatus as claimed in claim 1 wherein said resilient peripheral ring is hollow and adapted to be inflated to support said diaphragm and wherein said device further comprises means for introducing an inflating fluid into said ring whereby the un-inflated ring and diaphragm can be collapsed for insertion through the cervical canal and into the uterus where the peripheral ring can be inflated to expand and support the diaphragm and secure it in position within the uterus.

4. An apparatus as claimed in claim 3 and wherein said means for introducing an inflating fluid into said ring comprises an elongated tube communicating at one end with the interior of said ring and terminating at its other end in adaptor means for receiving inflating fluid under pressure.

5. An apparatus as claimed in claim 4 and wherein said adaptor means includes valve means for selectively preventing unwanted flow of inflating fluid from said ring.

6. An apparatus as claimed in claim 2 and wherein said means for introducing an inflating fluid into said elongated member comprises a flexible tube communicating at one end with the interior of said elongated member and terminating at its other end in adaptor means for coupling to a source of inflating fluid under pressure.

7. An apparatus as claimed in claim 2 and wherein said elongated member comprises a tubular latex rubber sac.

8. An apparatus as claimed in claim 7 and wherein said diaphragm is formed of latex rubber.

9. An apparatus as claimed in claim 8 and wherein said means for maintaining the diaphragm in position within the uterus comprises a resilient collapsible latex rubber ring bounding and supporting said diaphragm at the end of said tubular latex rubber sac.

10. An apparatus for use in the ultrasonographic determination and monitoring of the position of a fetal head and the configuration of the cervix during labor, said device comprising:
   an elongated tubular latex rubber sac adapted to be inserted within the vaginal cavity and inflated therein to bear against and conform to the shape of the vaginal cavity walls;
   a flexible latex rubber diaphragm closing one end of said tubular sac with said diaphragm being adapted to be inserted through the cervical canal and into the uterus to bear against and conform to the shape of at least a portion of a fetal head therein upon inflation of said tubular sac;
   means for maintaining said diaphragm in position within the uterus comprising a resilient collapsible ring bounding and supporting said diaphragm at the end of said sac with said ring being adapted to be collapsed for insertion of said ring and said diaphragm through the cervical canal and into the uterus where said ring can be released to expand and surround the cervical opening and lodge in place within the uterus; and
   means for introducing an inflating fluid into said tubular sac comprising an elongated tube communicating at one end with the interior of said sac and terminating at its other end in means for receiving inflating fluid under pressure, said tube being sized to extend to a location outside the mother's body when the device is in positioned within the birth canal.

11. A method determining the position of a fetal head and the configuration of the cervix during labor with said method comprising the steps of:
   (a) inserting an inflatable member into the birth canal with a first portion of the inflatable member positioned within the vaginal cavity, a second portion of the inflatable member extending through the cervical canal and a third portion of the inflatable member positioned within the uterus adjacent the fetal head;

(b) introducing an inflating fluid into the inflatable member to cause the inflatable member to expand and bear against the interior of the vaginal cavity, the cervix and cervical canal and the fetal head within the uterus;

(c) performing an ultrasonographic examination of the birth canal with the inflated member therein; and (d) analyzing the resulting ultrasound images to determine the position of the fetal head and the configuration of the cervix.

12. The method of claim 11 and wherein step (b) the inflating fluid has a sonic density that is different from the sonic density of surrounding tissue.

13. A sound wave transmission interface adapted to be coupled to a sound wave transmission and monitoring device and to be inserted into the birth canal for use during labor preceding child birth, said interface comprising a membrane for positioning within the uterus adjacent the fetal head, means for removably securing said membrane in position within the uterus, an elongated fluid containment means continuous with said membrane and adapted to extend therefrom through the cervical canal and into the vaginal cavity when said membrane is in position within the uterus, and means for introducing fluid into said fluid containment means for inflation thereof to provide an interface between said fluid containment means and surfaces of the vaginal cavity and cervix and between said membrane and at least a portion of the fetal head, said means for removably securing said membrane in position within the uterus comprising a resilient ring integrally formed with and bounding said membrane, said ring being adapted to be collapsed for insertion through the cervical canal and into the uterus and, once in the uterus, to be expanded to an annular shape to secure the membrane in position within the uterus.

14. The interface of claim 13 and wherein said ring is formed of resilient flexible material.

15. The interface of claim 13 wherein said ring is hollow and wherein said interface further comprises means for introducing an inflating fluid into said hollow ring when said ring and said membrane are positioned within the uterus to cause said ring to expand to an annular shape thereby securing the membrane in position within the uterus.

16. An apparatus for use in ultrasound determination and monitoring of the position of a fetal head and the configuration of the cervix and birth canal during labor, and apparatus comprising:

a flexible diaphragm sized to be inserted through the cervical canal and into the uterus to reside adjacent the head of a fetus therein;

a flexible expandable sleeve joined at one end to said diaphragm and extending rearwardly thereof, said sleeve and said diaphragm together forming a flexible sheath;

means at the junction of said diaphragm and said sleeve for retaining said diaphragm within the uterus adjacent a fetal head with said sleeve extending from said means through the cervical canal and through at least a portion of the vaginal cavity; and means for introducing an inflating fluid into said sleeve to cause said sleeve to expand and bear against the walls of the cervical canal and vaginal cavity and to cause said flexible diaphragm to bear against at least a portion of the fetal head within the uterus.

* * * * *